United States Patent
Lins et al.

(10) Patent No.: US 8,007,517 B2
(45) Date of Patent: Aug. 30, 2011

(54) INTERSPINOUS DISTRACTION DEVICES AND ASSOCIATED METHODS OF INSERTION

(75) Inventors: Robert E. Lins, Boca Raton, FL (US); Loren E. Lins, Boca Raton, FL (US); Harvey Simovitch, Boca Raton, FL (US)

(73) Assignee: Lanx, Inc., Broomfield, CO (US)

( * ) Notice: Subject to any disclaimer, the term of this patent is extended or adjusted under 35 U.S.C. 154(b) by 574 days.

(21) Appl. No.: 11/257,647

(22) Filed: Oct. 25, 2005

(65) Prior Publication Data

US 2006/0089654 A1 Apr. 27, 2006

Related U.S. Application Data

(60) Provisional application No. 60/621,712, filed on Oct. 25, 2004.

(51) Int. Cl.
*A61B 17/70* (2006.01)
(52) U.S. Cl. .......................... 606/248; 606/279
(58) Field of Classification Search ............... 623/17.11, 623/17.12, 17.13, 17.14, 17.15, 17.16; 606/248, 606/249, 279
See application file for complete search history.

(56) References Cited

U.S. PATENT DOCUMENTS

| | | | |
|---|---|---|---|
| 2,677,369 A | 4/1954 | Knowles | |
| 2,789,660 A | 4/1957 | Knowles | |
| 4,092,788 A | 6/1978 | Gowing | |
| 4,369,770 A | 1/1983 | Bacal et al. | |
| 4,409,968 A | 10/1983 | Drummond | |
| 4,448,191 A | 5/1984 | Rodnyansky et al. | |
| 4,636,217 A * | 1/1987 | Ogilvie et al. | 623/17.11 |
| 5,010,879 A | 4/1991 | Moriya et al. | |
| 5,472,426 A * | 12/1995 | Bonati et al. | 604/164.1 |
| 5,496,318 A | 3/1996 | Howland et al. | |
| 5,503,617 A | 4/1996 | Jako | |
| 5,609,634 A | 3/1997 | Voydeville | |
| 5,645,599 A | 7/1997 | Samani | |
| 5,658,335 A | 8/1997 | Allen | |
| 5,800,550 A | 9/1998 | Sertich | |
| 5,813,978 A | 9/1998 | Jako | |
| 5,836,948 A | 11/1998 | Zucherman et al. | |

(Continued)

FOREIGN PATENT DOCUMENTS

EP 1 266 606 A2 12/2002

(Continued)

OTHER PUBLICATIONS

Zuckerman et al. "Spine Distraction Implant" U.S. Patent Application Publication US 2001/0012938, Published Aug. 9, 2001.

(Continued)

*Primary Examiner* — Eduardo C Robert
*Assistant Examiner* — Jan Christopher Merene
(74) *Attorney, Agent, or Firm* — Holland & Hart LLP (57) ABSTRACT

In various exemplary embodiments, the present invention provides a plurality of novel interspinous distraction devices and associated methods of insertion. The interspinous distraction devices of the present invention are designed and configured to effectively treat such conditions as lumbar spinal stenosis and degenerative disc disease. Advantageously, the interspinous distraction devices of the present invention may be inserted through conventional open procedures, typically requiring a relatively large incision and a general anesthetic, or through novel minimally-invasive procedures, typically requiring only a local anesthetic. These novel minimally-invasive procedures and related enabling devices are also disclosed and described herein.

11 Claims, 8 Drawing Sheets

U.S. PATENT DOCUMENTS

| | | | |
|---|---|---|---|
| 5,860,977 A | 1/1999 | Zucherman et al. | |
| 5,876,404 A | 3/1999 | Zucherman et al. | |
| 6,045,552 A | 4/2000 | Zucherman et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,090,112 A | 7/2000 | Zucherman et al. | |
| 6,149,652 A | 11/2000 | Zucherman et al. | |
| 6,152,926 A | 11/2000 | Zucherman et al. | |
| 6,156,038 A | 12/2000 | Zucherman et al. | |
| 6,183,471 B1 | 2/2001 | Zucherman et al. | |
| 6,190,387 B1 | 2/2001 | Zucherman et al. | |
| 6,200,322 B1* | 3/2001 | Branch et al. | 606/96 |
| 6,235,030 B1 | 5/2001 | Zucherman et al. | |
| 6,238,397 B1 | 5/2001 | Zucherman et al. | |
| 6,277,094 B1 | 8/2001 | Schendel | |
| 6,280,444 B1 | 8/2001 | Zucherman et al. | |
| 6,332,882 B1 | 12/2001 | Zucherman et al. | |
| 6,332,883 B1 | 12/2001 | Zucherman et al. | |
| 6,379,355 B1 | 4/2002 | Zucherman et al. | |
| 6,398,811 B1* | 6/2002 | McKay | 623/17.16 |
| 6,416,776 B1 | 7/2002 | Shamie | |
| 6,419,676 B1 | 7/2002 | Zucherman et al. | |
| 6,419,677 B2 | 7/2002 | Zucherman et al. | |
| 6,440,169 B1 | 8/2002 | Elberg et al. | |
| 6,451,019 B1 | 9/2002 | Zucherman et al. | |
| 6,451,020 B1 | 9/2002 | Zucherman et al. | |
| 6,451,021 B1 | 9/2002 | Ralph et al. | |
| 6,478,796 B2 | 11/2002 | Zucherman et al. | |
| 6,500,178 B2 | 12/2002 | Zucherman et al. | |
| 6,514,256 B2 | 2/2003 | Zucherman et al. | |
| 6,520,907 B1 | 2/2003 | Foley et al. | |
| 6,582,433 B2 | 6/2003 | Yun | |
| 6,599,294 B2 | 7/2003 | Fuss et al. | |
| 6,626,944 B1 | 9/2003 | Taylor | |
| 6,652,527 B2 | 11/2003 | Zucherman et al. | |
| 6,652,534 B2 | 11/2003 | Zucherman et al. | |
| 6,679,833 B2 | 1/2004 | Smith et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,712,819 B2 | 3/2004 | Zucherman et al. | |
| 6,733,534 B2 | 5/2004 | Sherman | |
| 6,746,485 B1 | 6/2004 | Zucherman et al. | |
| 6,761,720 B1 | 7/2004 | Senegas | |
| 6,796,983 B1 | 9/2004 | Zucherman et al. | |
| 6,800,084 B2 | 10/2004 | Davison et al. | |
| 6,902,566 B2 | 6/2005 | Zucherman et al. | |
| 6,926,728 B2 | 8/2005 | Zucherman et al. | |
| 6,966,929 B2 | 11/2005 | Mitchell | |
| 6,989,011 B2 | 1/2006 | Paul et al. | |
| 7,029,473 B2 | 4/2006 | Zucherman et al. | |
| 7,083,649 B2 | 8/2006 | Zucherman et al. | |
| 7,087,083 B2* | 8/2006 | Pasquet et al. | 623/17.11 |
| 7,442,208 B2* | 10/2008 | Mathieu et al. | 623/17.11 |
| 2001/0007073 A1 | 7/2001 | Zucherman et al. | |
| 2001/0016743 A1 | 8/2001 | Zucherman et al. | |
| 2001/0016776 A1 | 8/2001 | Zuckerman et al. | |
| 2001/0021850 A1 | 9/2001 | Zucherman et al. | |
| 2001/0039452 A1 | 11/2001 | Zucherman et al. | |
| 2002/0095154 A1* | 7/2002 | Atkinson et al. | 606/61 |
| 2002/0183746 A1 | 12/2002 | Zucherman et al. | |
| 2003/0045935 A1* | 3/2003 | Angelucci et al. | 623/17.11 |
| 2003/0065330 A1 | 4/2003 | Zucherman et al. | |
| 2003/0083688 A1* | 5/2003 | Simonson | 606/191 |
| 2003/0153915 A1 | 8/2003 | Nekozuka | |
| 2003/0216736 A1 | 11/2003 | Robinson et al. | |
| 2004/0024458 A1 | 2/2004 | Senegas et al. | |
| 2004/0059339 A1 | 3/2004 | Roehm, III et al. | |
| 2004/0093001 A1 | 5/2004 | Hamada | |
| 2004/0106995 A1 | 6/2004 | Le Couedic et al. | |
| 2004/0138749 A1 | 7/2004 | Zucherman et al. | |
| 2004/0138750 A1 | 7/2004 | Mitchell | |
| 2004/0143270 A1 | 7/2004 | Zucherman et al. | |
| 2004/0147937 A1 | 7/2004 | Dunbar | |
| 2004/0153071 A1 | 8/2004 | Zucherman et al. | |
| 2004/0162617 A1 | 8/2004 | Zucherman et al. | |
| 2004/0167520 A1 | 8/2004 | Zucherman et al. | |
| 2004/0172135 A1 | 9/2004 | Mitchell | |
| 2004/0193159 A1 | 9/2004 | Zucherman et al. | |
| 2004/0199121 A1 | 10/2004 | Wenchell | |
| 2004/0199168 A1 | 10/2004 | Bertagnoli et al. | |
| 2004/0220568 A1 | 11/2004 | Zucherman et al. | |
| 2004/0249379 A1 | 12/2004 | Winslow et al. | |
| 2005/0010296 A1 | 1/2005 | Mitchell | |
| 2005/0010298 A1 | 1/2005 | Zucherman et al. | |
| 2005/0101955 A1 | 5/2005 | Zucherman et al. | |
| 2005/0113926 A1 | 5/2005 | Zucherman et al. | |
| 2005/0125065 A1 | 6/2005 | Zucherman et al. | |
| 2005/0143738 A1 | 6/2005 | Zucherman et al. | |
| 2005/0143820 A1 | 6/2005 | Zucherman et al. | |
| 2005/0143826 A1 | 6/2005 | Zucherman et al. | |
| 2005/0149192 A1 | 7/2005 | Zucherman et al. | |
| 2005/0149193 A1 | 7/2005 | Zucherman et al. | |
| 2005/0149196 A1 | 7/2005 | Zucherman et al. | |
| 2005/0154462 A1 | 7/2005 | Zucherman et al. | |
| 2005/0165398 A1* | 7/2005 | Reiley | 606/61 |
| 2005/0192586 A1 | 9/2005 | Zucherman et al. | |
| 2005/0196420 A1 | 9/2005 | Zucherman et al. | |
| 2005/0203512 A1* | 9/2005 | Hawkins et al. | 606/61 |
| 2005/0209603 A1 | 9/2005 | Zucherman et al. | |
| 2005/0216087 A1 | 9/2005 | Zucherman et al. | |
| 2005/0228383 A1 | 10/2005 | Zucherman et al. | |
| 2005/0228384 A1 | 10/2005 | Zucherman et al. | |
| 2005/0245929 A1* | 11/2005 | Winslow et al. | 606/61 |
| 2005/0261768 A1 | 11/2005 | Trieu | |
| 2006/0015099 A1 | 1/2006 | Cannon et al. | |
| 2006/0106397 A1* | 5/2006 | Lins | 606/90 |
| 2006/0247623 A1* | 11/2006 | Anderson et al. | 606/61 |
| 2007/0032790 A1* | 2/2007 | Aschmann et al. | 606/61 |
| 2007/0213829 A1* | 9/2007 | Le Couedic et al. | 623/17.16 |
| 2008/0058937 A1* | 3/2008 | Malandain et al. | 623/17.11 |

FOREIGN PATENT DOCUMENTS

| | | |
|---|---|---|
| JP | 2003220071 A | 8/2003 |
| WO | WO 94/00062 | 1/1994 |
| WO | WO 2005/009300 A1 | 2/2005 |

OTHER PUBLICATIONS

Zucherman et al., "Supplemental Spine Fixation Device and Methods" U.S. Patent Application Publication US 2002/0029039, Published Mar. 7, 2002.

Nekozuka et al., "Vertebral Body Distance Retainer" U.S. Patent Application Publication US 2003/0153915, Published Aug. 14, 2003.

Robinson et al, "Device for Fixation of Spinous Processes", U.S. Patent Application Publication US 2003/0216736, Published Nov. 20, 2003.

International Bureau, Notification Concerning Transmittal of International Preliminary Report on Patentability (Chapter 1 of the Patent Cooperation Treaty), May 10, 2007.

KYPHON "X-Stop A Patient's Guide Lumbar Spinal Stedosis & X-Stop Interspinous Decompress".

Jeremy C Wang, MD. Regis W. Haid Jr., M.D, Jay S. Miller, M.D. and James C. Robinson, M.D "Comparison of CD Horizon Spire spinous process plate stabilization and pedicle screw fixation after anterior lumbar interbody fusion" Feb. 4, 2006.

Jeremy C Wang, MD., David Spenciner, P.E., Sc.M., and James C. Robinson, M.D. "Spire spinous process stabilization plate: biochemical evaluation of a novel technology" Feb. 4, 2006.

Ole Bostman, Pertti Myllynen & Erik B. Riska "Posterior spinal fusion using internal fixation with the Daab plate" pp. 310-314 1984.

F.L. Knowles "The Knowles Vertebral Support Orientation" pp. 551-554, Oct. 1958.

KYPHON "X-Stop IPD System The first minimally invasive solution to lumbar spine stenosis".

Lee, Jangbo, et al. "An Interspinous Process Distractor (X Stop) for Lumbar Spinal Stenosis in Elderly Patients", J. Spinal Disord Tech., vol. 17, No. 1, Feb. 2004, pp. 72-77.

\* cited by examiner

INTERSPINOUS DISTRACTION DEVICES AND ASSOCIATED METHODS OF INSERTION

CROSS-REFERENCE TO RELATED APPLICATION(S)

The present non-provisional patent application claims the benefit of priority of U.S. Provisional Patent Application No. 60/621,712, entitled "INTERSPINOUS DISTRACTION DEVICES AND ASSOCIATED METHODS OF INSERTION," and filed on Oct. 25, 2004, which is incorporated in full by reference herein.

FIELD OF THE INVENTION

The present invention relates generally to the medical and surgical fields. More specifically, the present invention relates to a plurality of novel interspinous distraction devices and associated methods of insertion. The interspinous distraction devices of the present invention are designed and configured to effectively treat such conditions as lumbar spinal stenosis and degenerative disc disease. Advantageously, the interspinous distraction devices of the present invention may be inserted through conventional open procedures, typically requiring a relatively large incision and a general anesthetic, or through novel minimally-invasive procedures, typically requiring only a local anesthetic. These novel minimally-invasive procedures and related enabling devices are also disclosed and described herein.

BACKGROUND OF THE INVENTION

Lumbar spinal stenosis is characterized by a tightening of or decrease in the cross-sectional diameter of the spinal canal and neural foramen, through which the spinal cord and nerve roots of the lumbar (lower) spine pass, caused by the degeneration of the lumbar discs (through fluid loss and collapse) and the facet joints of the spinal column. In lumbar spinal stenosis, the lumbar discs deteriorate and the lumbar disc spaces collapse, resulting in a portion of the lumbar discs protruding into the ventral or anterior (front) portion of the spinal canal. At the same time, the two facet joints associated with each lumbar vertebrae become arthritic, growing in size, and protruding into the dorsal or posterior (back) portion of the spinal canal. Thus, the cross-sectional diameter of the spinal canal is decreased, impinging on the spinal cord and nerve roots of the lumbar spine. In addition, the ligamentum flavum that connect the bases of the spinous processes of the spinal column and the lamina tend to buckle with lumbar disc collapse, further decreasing the cross-sectional diameter of the spinal canal. The neural foramen, through which the nerve roots exit, are pinched with disc collapse and facet joint arthropathy. This condition is especially common in the elderly and symptoms may include remitting or unremitting pain and/or weakness/numbness in the middle to lower back and/or legs when moving and/or stationary. It should be noted that similar problems can occur in the cervical (upper) spine as well.

Conventional treatments for lumbar spinal stenosis include oral and/or injectable analgesic and/or anti-inflammatory medications (non-steroidal and/or steroidal), activity avoidance and/or physical therapy, braces, and/or surgical procedures. Surgical procedures for lumbar spinal stenosis include laminectomies/laminotomies and/or spinal fusions. In a laminectomy/laminotomy, all or a portion of a given facet joint, lamina, and ligamentum flavum are removed to alleviate compression of the spinal canal. This procedure basically "unroofs" or enlarges a portion of the spinal canal. Additionally, a spinal fusion may be performed. In a spinal fusion, a connecting bar and a bone graft are used to join or fuse adjacent vertebrae via a plurality of pedicle screws, thus stabilizing the vertebral segment. Much, if not all, of a given lumbar disc is removed in conjunction with a spinal fusion. In general, a spinal fusion is most suitable when there is instability or translation between adjacent vertebrae (spondylolisthesis). Disadvantageously, the plurality of pedicle screws used to perform a spinal fusion may become loose with the passage of time if a nonunion develops. Both laminectomies/laminotomies and spinal fusions are major, open procedures, typically requiring a relatively large incision and a general anesthetic. This may be dangerous for the elderly or the sick. In addition, both procedures are very expensive.

What has been observed clinically is that many patients, when they flex forward, experience an increase in the cross-sectional diameter of the spinal canal and neural foramen, thus alleviating or eliminating their pain and/or weakness/numbness caused by lumbar spinal stenosis. This is caused by the temporary distraction of the spinous processes and the "stretching out" of the ligamentum flavum that connect the bases of the spinous processes and lamina. The collapsed neural foramen are also increased in height and cross-sectional area by the distraction. In other words, the lumbar discs and other structures of the spinal column are temporarily decompressed. This observation has led to improved treatments for lumbar spinal stenosis.

The interspinous process distractor for lumbar spinal stenosis disclosed and described by Lee et al. (J. Spinal Disord. Tech., Vol. 17, No. 1, February 2004) provides a main body assembly including a spacer and a universal wing assembly. The main body assembly is disposed between adjacent interspinous processes, distracting them, and the universal wing assembly is used to lock the main body assembly in place. Because the interspinous process distractor utilizes a nut that must be engaged and tightened, the interspinous process distractor must be inserted using a conventional open procedure. Again, this may be dangerous for the elderly or the sick and requires a general anesthetic. Other conventional interspinous process distractors known to those of ordinary skill in the art suffer the same shortcoming.

Thus, what is needed are simple, inexpensive interspinous distraction devices and associated methods of insertion that are designed and configured to effectively treat such conditions as lumbar spinal stenosis. The interspinous distraction devices should be capable of being inserted through conventional open procedures, typically requiring a relatively large incision and a general anesthetic, or through novel minimally-invasive procedures, typically requiring only a local anesthetic.

BRIEF SUMMARY OF THE INVENTION

In various embodiments, the present invention provides a plurality of novel interspinous distraction devices and associated methods of insertion. The interspinous distraction devices of the present invention are designed and configured to effectively treat such conditions as lumbar spinal stenosis and degenerative disc disease. Advantageously, the interspinous distraction devices of the present invention may be inserted through conventional open procedures, typically requiring a relatively large incision and a general anesthetic, or through novel minimally-invasive procedures, typically requiring only a local anesthetic. These novel minimally-invasive procedures and related enabling devices are also disclosed and described herein.

In one exemplary embodiment of the present invention, an interspinous distraction device for treating such conditions as lumbar spinal stenosis includes a body assembly configured to be disposed between adjacent spinous processes of the spinal column of a patient, wherein the body assembly is sized such that the body assembly distracts the adjacent spinous processes apart. The interspinous distraction device also includes a plurality of attachment arms selectively extending outwardly from the body assembly in the direction of each of the adjacent spinous processes, the plurality of attachment arms configured to be disposed about a portion of each of the adjacent spinous processes and securely hold the body assembly in place relative to each of the adjacent spinous processes of the spinal column of the patient.

In another exemplary embodiment of the present invention, a dilation tube system for providing minimally-invasive surgical access to a portion of the spinal column or the like includes a hollow dilation tube having a first end, a second end, a given cross-sectional shape, and a longitudinal axis, wherein the first end of the dilation tube includes a cut-away portion for providing access from an interior portion of the dilation tube to an exterior portion of the dilation tube in a direction perpendicular to the longitudinal axis of the dilation tube. The dilation tube system also includes a hollow guide tube having a first end, a second end, a given cross-sectional shape, and a longitudinal axis disposed concentrically within the dilation tube, wherein the first end of the dilation tube includes an elbow portion for providing access from an interior portion of the guide tube to an exterior portion of the guide tube in a direction perpendicular to the longitudinal axis of the guide tube through the cut-away portion of the dilation tube. The dilation tube system further includes a plurality of additional hollow dilation tubes having graduated diameters.

In a further exemplary embodiment of the present invention, a method for inserting an interspinous distraction device for treating such conditions as lumbar spinal stenosis includes disposing a body assembly between adjacent spinous processes of the spinal column of a patient, wherein the body assembly is sized such that the body assembly distracts the adjacent spinous processes apart. The method for inserting the interspinous distraction device also includes extending a plurality of attachment arms outwardly from the body assembly, the plurality of attachment arms disposed about a portion of each of the adjacent spinous processes and securely holding the body assembly in place relative to each of the adjacent spinous processes of the spinal column of the patient. Optionally, the body assembly is disposed between adjacent spinous processes of the spinal column of the patient through a hollow dilation tube having a first end, a second end, a given cross-sectional shape, and a longitudinal axis, wherein the first end of the dilation tube includes a cut-away portion for providing access from an interior portion of the dilation tube to an exterior portion of the dilation tube in a direction perpendicular to the longitudinal axis of the dilation tube. Optionally, the body assembly is also disposed between adjacent spinous processes of the spinal column of the patient through a hollow guide tube having a first end, a second end, a given cross-sectional shape, and a longitudinal axis disposed concentrically within the dilation tube, wherein the first end of the dilation tube includes an elbow portion for providing access from an interior portion of the guide tube to an exterior portion of the guide tube in a direction perpendicular to the longitudinal axis of the guide tube through the cut-away portion of the dilation tube.

In a still further exemplary embodiment of the present invention, an interspinous distraction device for treating such conditions as lumbar spinal stenosis and degenerative disc disease includes a body assembly configured to be disposed between adjacent spinous processes of the spinal column of a patient, wherein the body assembly is sized such that the body assembly distracts the adjacent spinous processes apart. The interspinous distraction device also includes a band configured to be disposed about the adjacent spinous processes of the spinal column of the patient and engage the body assembly, wherein the band is sized such that the adjacent spinous processes are stabilized with respect to one another.

In a still further exemplary embodiment of the present invention, a tool for inserting an interspinous distraction device through a dilation tube having a laterally-oriented opening includes a shaft portion having a first end and a second end; a handle portion attached to the first end of the shaft portion; and a cutting portion attached to the second end of the shaft portion, the cutting portion including a cutting edge that is substantially directed towards the first end of the shaft portion.

In a still further exemplary embodiment of the present invention, a tool for inserting an interspinous distraction device through a dilation tube having a laterally-oriented opening includes a shaft portion having a first end and a second end; a handle portion attached to the first end of the shaft portion; and a plurality of paddles attached to the second end of the shaft portion, the plurality of paddles operable for distracting apart adjacent spinous processes of a spinal column of a patient in response to selective actuation of the handle portion.

In a still further exemplary embodiment of the present invention, a tool for inserting an interspinous distraction device through a dilation tube having a laterally-oriented opening includes a shaft portion having a first end and a second end; a handle portion attached to the first end of the shaft portion; and a sizing portion attached to the second end of the shaft portion, the sizing portion selectively sized to fit between adjacent spinous processes of a spinal column of a patient, thereby determining the size of a space between the adjacent spinous processes of the spinal column of the patient.

BRIEF DESCRIPTION OF THE DRAWINGS

The present invention is illustrated and described herein with reference to various figures, in which like reference numbers denote like components and/or parts, and in which.

DETAILED DESCRIPTION OF THE INVENTION

In various exemplary embodiments, the present invention provides a plurality of novel interspinous distraction devices and associated methods of insertion. The interspinous distraction devices of the present invention are designed and configured to effectively treat such conditions as lumbar spinal stenosis and degenerative disc disease. Advantageously, the interspinous distraction devices of the present invention may be inserted through conventional open procedures, typically requiring a relatively large incision and a general anesthetic, or through novel minimally-invasive procedures, typically requiring only a local anesthetic. These novel minimally-invasive procedures, and related enabling devices, are also disclosed and described herein.

Figure 1:
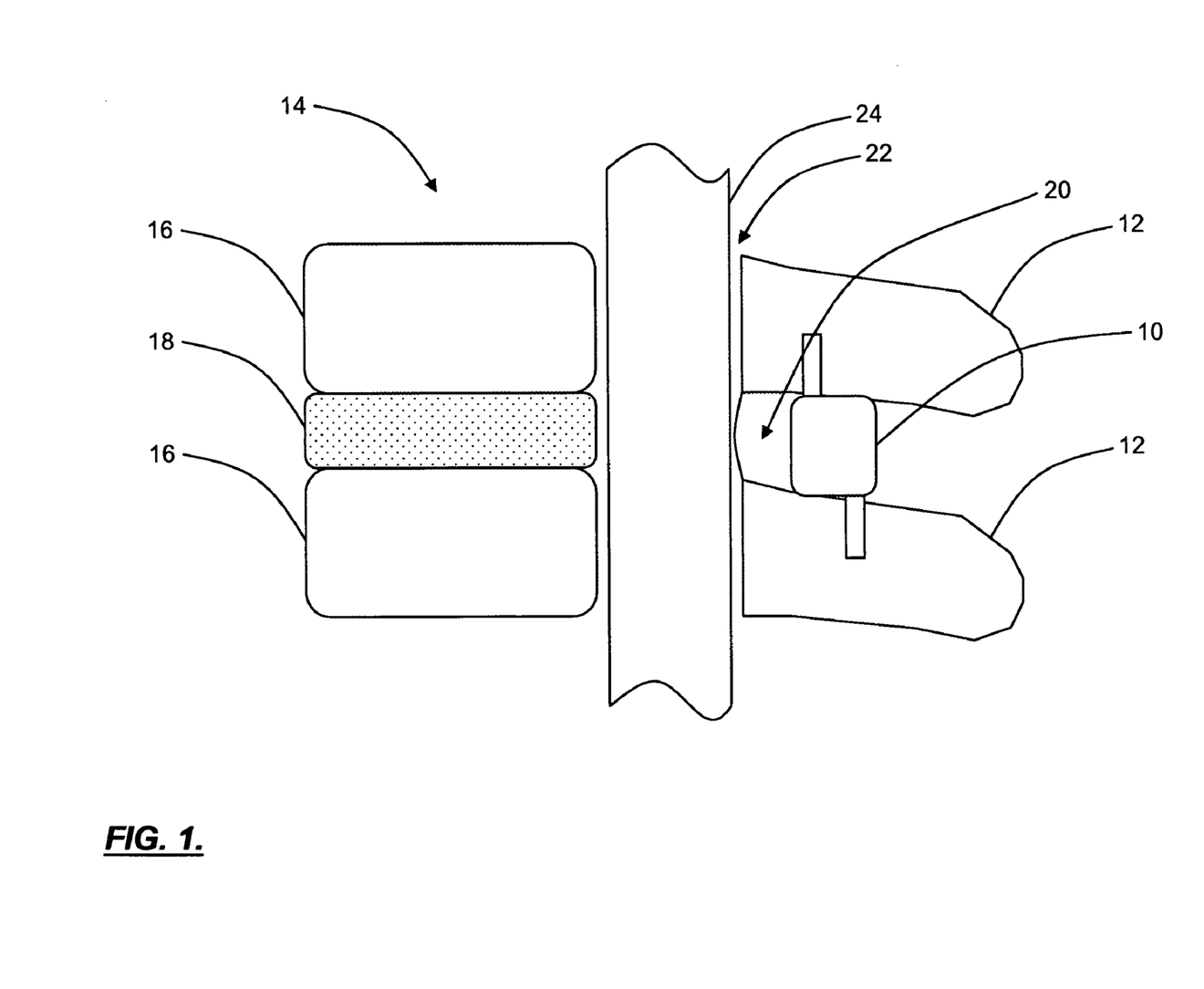
FIG. 1 is a cross-sectional side view illustrating the spinal column of a patient and the placement of one exemplary embodiment of the interspinous distraction device of the present invention.

Referring now to FIG. 1, in one exemplary embodiment, the interspinous distraction device 10 of the present invention is disposed between adjacent spinous processes 12 of the spinal column 14 of a patient. The spinal column 14 also includes a plurality of vertebral bodies 16 present on a plurality of levels of the lumbar (lower) and cervical (upper) spine and a plurality of discs 18 separating the plurality of vertebral bodies 16. It is these discs 18 and the facet joints 20 associated with the ligamentum flavum that deteriorate and protrude into the spinal canal 22, impinging on the spinal cord 24 and neural foramen, in conditions such as lumbar spinal stenosis. The interspinous distraction device 10 is sized such that it distracts adjacent spinous processes 12 apart, alleviating the protrusion and impingement described above.

Figure 2:
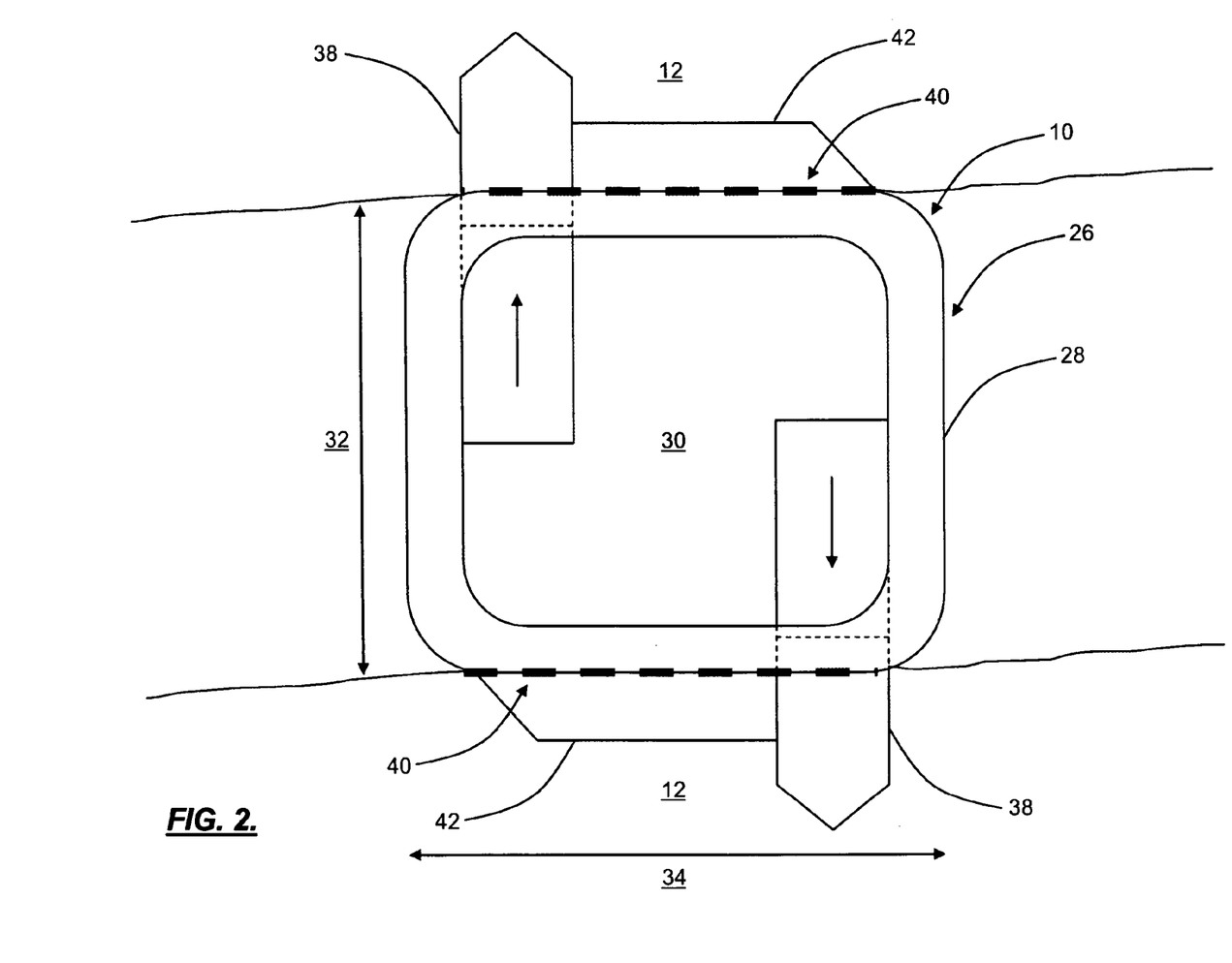
FIG. 2 is a cross-sectional side view illustrating one exemplary embodiment of the interspinous distraction device of the present invention.
Figure 3:
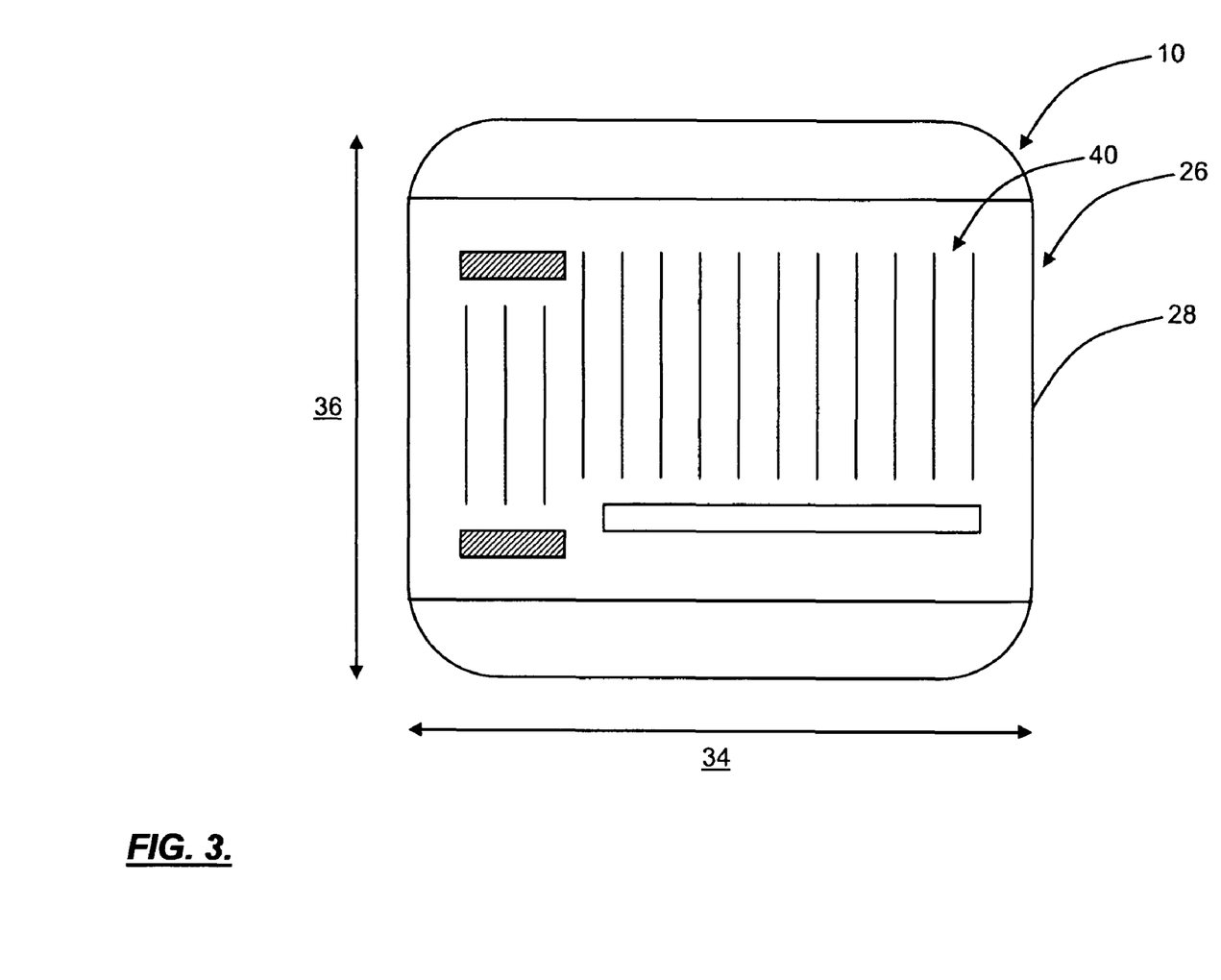
FIG. 3 is a planar top view illustrating the interspinous distraction device of FIG. 2.
Figure 4:
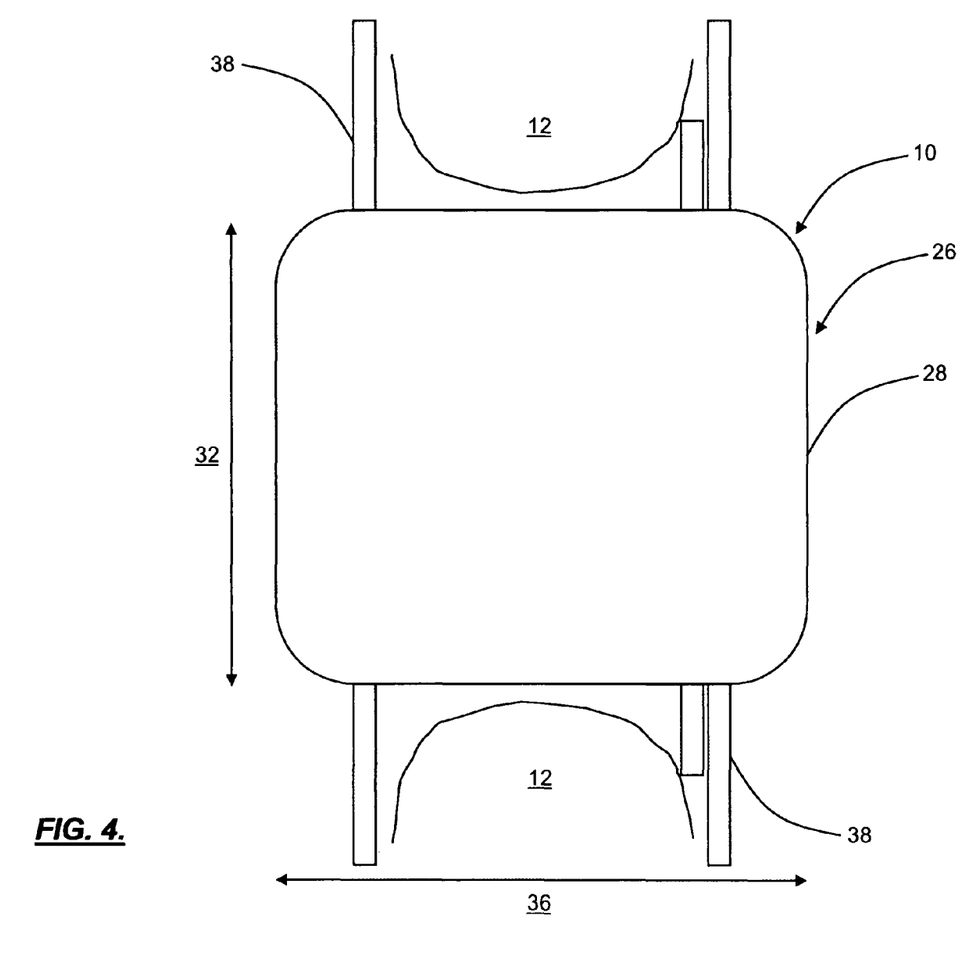
FIG. 4 is a planar front view illustrating the interspinous distraction device of FIGS. 2 and 3.

Referring now to FIGS. 2-4, the interspinous distraction device 10 of the present invention includes a body assembly 26 consisting of a circumferential wall 28 defining an interior void 30. The body assembly 26 has a shape that is substantially rectangular, substantially square, substantially oval, substantially circular, a combination thereof, or any other suitable shape. The body assembly 26 has a height 32 of between about 4 mm and about 20 mm, a width 34 of between about 10 mm and about 25 mm, and a thickness 36 of between about 10 mm and about 20 mm. Preferably, the body assembly 26 and other components of the interspinous distraction device 10 are made of a medically-implantable, corrosion-resistant metal; a medically-implantable, corrosion-resistant metal alloy; a medically-implantable plastic; a medically-implantable ceramic; or a combination thereof.

The body assembly 26 of the interspinous distraction device 10 also includes a plurality of attachment arms 38 selectively extending outwardly from the circumferential wall 28 of the body assembly 26 in the direction of each of the adjacent spinous processes 12, the plurality of attachment arms 38 configured to be disposed about a portion of each of the adjacent spinous processes 12 and securely hold the body assembly 26 in place relative to each of the adjacent spinous processes 12. Preferably, each of the plurality of attachment arms 38 is at least partially disposed within the interior void 30 defined by the circumferential wall 28 of the body assembly 26 and is selectively extendable outwardly from/retractable inwardly into the interior void 30. Each of the plurality of attachment arms 38 has a length of between about 4 mm and about 20 mm. In one exemplary embodiment of the interspinous distraction device 10 of the present invention, the plurality of attachment arms 38 resemble a plurality of staple-like structures. Optionally, the body assembly 26 of the interspinous distraction device 10 incorporates a filler plug (not shown) selectively disposed within the interior void 30 defined by the circumferential wall 28 when the plurality of attachment arms 38 have been extended.

The body assembly 26 of the interspinous distraction device 10 further includes one or more friction surfaces 40 consisting of one or more ridged surfaces, one or more grooved surfaces, one or more corrugated surfaces, one or more pebbled surfaces, or a combination thereof, the one or more friction surfaces 40 configured to securely hold the body assembly 26 in place relative to each of the adjacent spinous processes 12.

The body assembly 26 of the interspinous distraction device 10 still further includes one or more fin structures 42 also configured to securely hold the body assembly 26 in place relative to each of the adjacent spinous processes 12. Specifically, the one or more fin structures 42 prevent the body assembly 26 from "overshooting" the gap between the adjacent spinous processes 12 when the interspinous distraction device 10 is inserted. The one or more fin structures 42 may be of any suitable size and/or shape to achieve this purpose.

Although one specific embodiment of the interspinous distraction device 10 of the present invention has been illustrated and described above, other embodiments may perform similar functions and/or achieve similar results. For example, the body assembly 26 and the plurality of attachment arms 38 of the interspinous distraction device 10 may be configured such that the plurality of attachment arms 38 rotatably engage the adjacent spinous processes 12 when the body assembly 26 is rotated.

Figure 5:
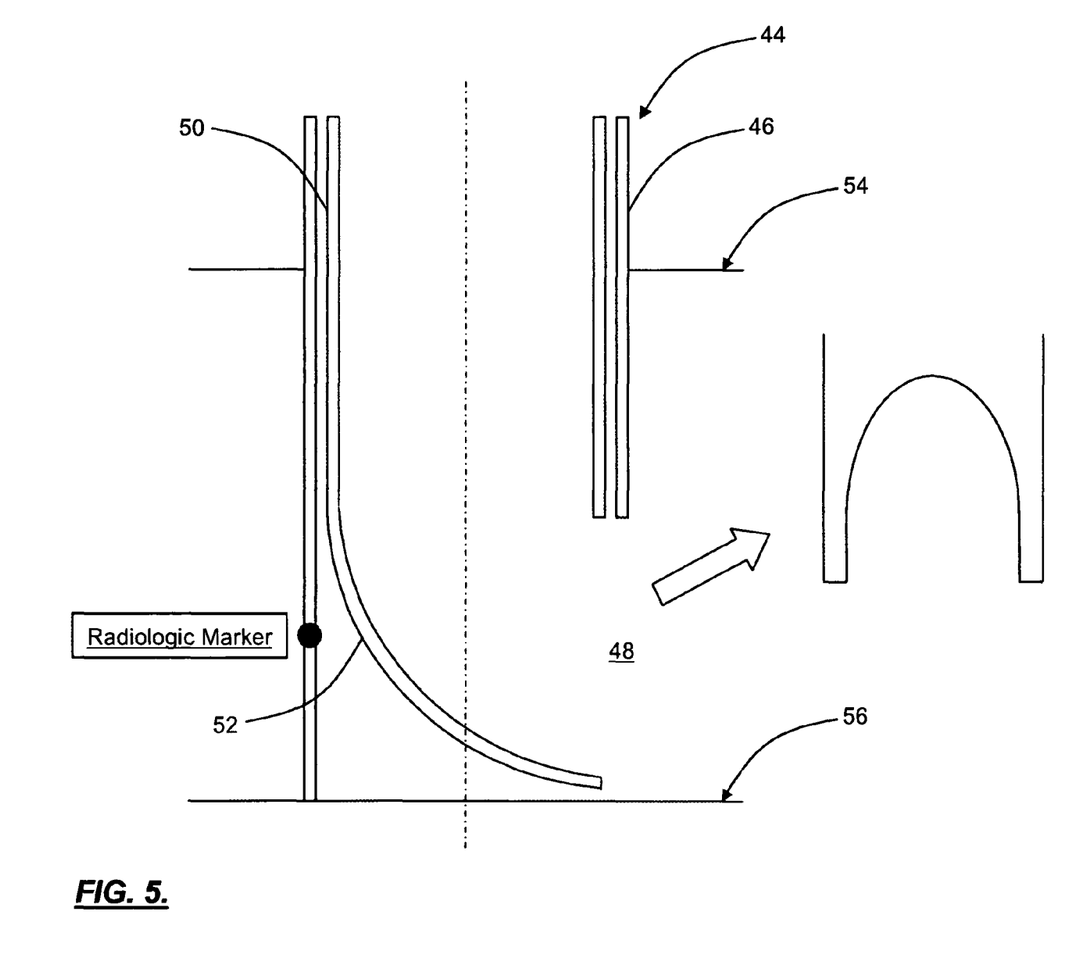
FIG. 5 is a longitudinal cross-sectional side view illustrating one exemplary embodiment of the dilation tube system of the present invention, the dilation tube system used to insert the interspinous distraction device of FIGS. 2-4 into the spinal column of a patient.

Referring now to FIG. 5, in one exemplary embodiment, the dilation tube system 44 of the present invention provides minimally-invasive surgical access to a portion of the spinal column or the like. The dilation tube system 44 includes a hollow dilation tube 46 having a first end, a second end, a given cross-sectional shape, and a longitudinal axis. The first end of the dilation tube 46 includes a cut-away portion 48 for providing access from an interior portion of the dilation tube 46 to an exterior portion of the dilation tube 46 in a direction perpendicular to the longitudinal axis of the dilation tube 46.

The dilation tube system 44 also includes a hollow guide tube 50 having a first end, a second end, a given cross-sectional shape, and a longitudinal axis. The hollow guide tube 50 is disposed concentrically within the dilation tube 46. The first end of the guide tube 50 includes an elbow portion 52 for providing access from an interior portion of the guide tube 50 to an exterior portion of the guide tube 50 in a direction perpendicular to the longitudinal axis of the guide tube 50 through the cut-away portion 48 of the dilation tube 46.

The dilation tube 46 and the guide tube 50 each have a cross-sectional shape that is substantially circular, substantially semi-circular, substantially oval, substantially square, substantially rectangular, substantially triangular, a combination thereof, or any other suitable shape. The dilation tube 46 and the guide tube 50 each have a diameter of between about 18 mm and about 22 mm. The dilation tube 46 and the guide tube 50 are each made of a material such as a medically-implantable, corrosion-resistant metal; a medically-implantable, corrosion-resistant metal alloy; a medically-implantable plastic; a medically-implantable ceramic; a combination thereof; or the like.

In operation, the dilation tube 46 and the guide tube 50 are inserted through the skin 54 of a patient, as described in greater detail below, and seated in an area of interest or on a surface of interest 56. The dilation tube 46 provides access to the area of interest and the cut-away portion 48 of the dilation tube 46 provides access to the area of interest in a direction perpendicular to the longitudinal axis of the dilation tube 46. Likewise, the guide tube 50 provides access to the area of interest and the elbow portion 52 of the guide tube 50 provides access to the area of interest in a direction perpendicular to the longitudinal axis of the guide tube 50. In other words, the dilation tube 46 and the guide tube 50 of the present invention provide novel lateral access to an area of interest. Advantageously, the elbow portion 52 of the guide tube 50 helps to guide devices and instruments inserted through the guide tube 50 into a lateral position for placement.

Figure 6:
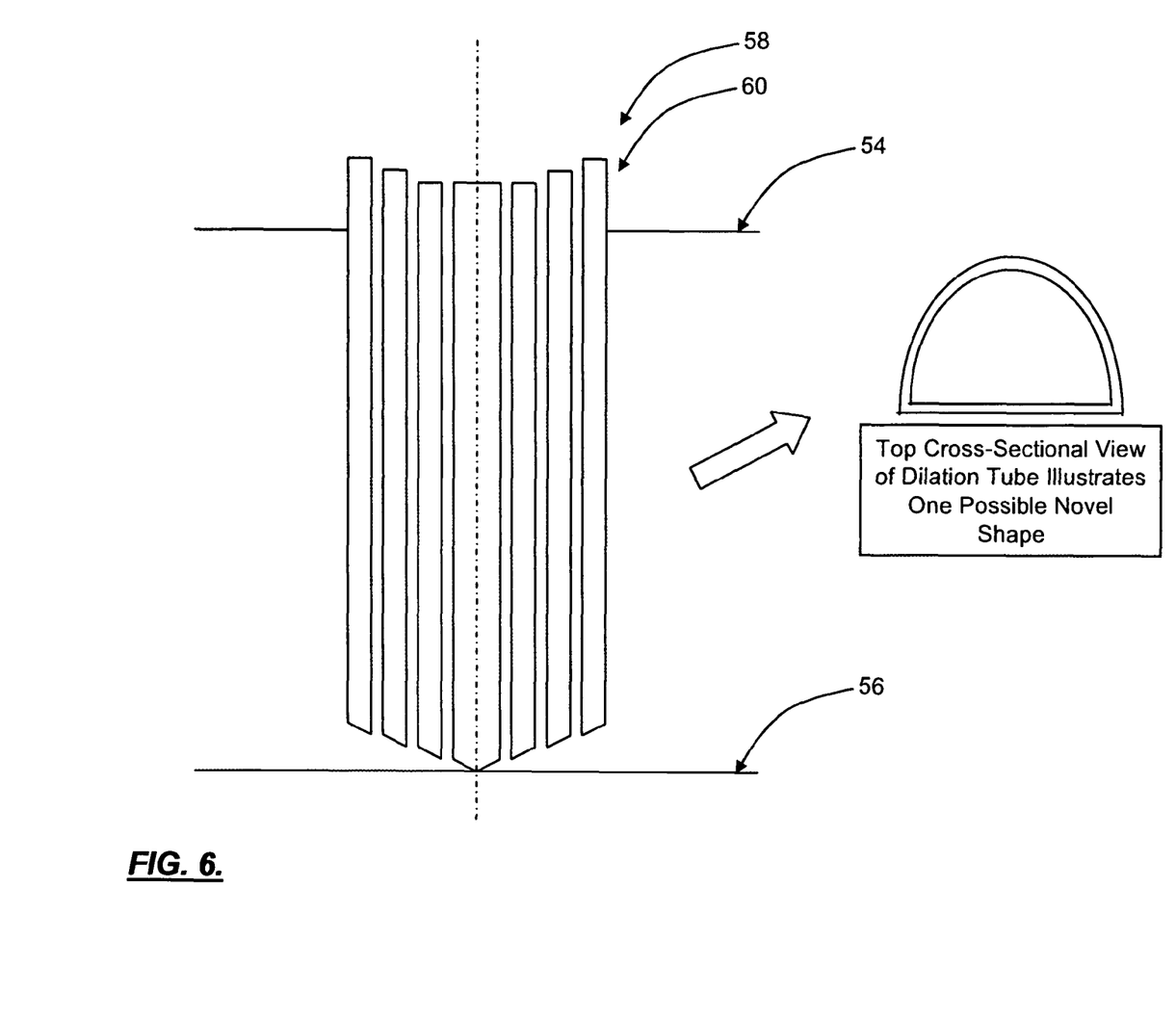
FIG. 6 is a longitudinal cross-sectional side view illustrating a conventional dilation tube system used in conjunction with the dilation tube system of FIG. 5, as well as a novel cross-sectional shape of the dilation tube system.

Referring now to FIG. 6, the dilation tube system 44 of the present invention is preferably used in conjunction with a conventional dilation tube system 58, well known to those of ordinary skill in the art, that includes a plurality of additional dilation tubes 60, each of the plurality of additional dilation 60 tubes having a diameter that is smaller than the diameter of the dilation tube 46 of the present invention. Each of the plurality of additional dilation tubes 60 is selectively and temporarily disposed concentrically within a space or hole of increasing diameter that is eventually large enough to receive the dilation tube 46 and guide tube 50 of the present invention.

In one exemplary embodiment of the present invention, a method for inserting the interspinous distraction device 10 (FIGS. 2-4) described above includes disposing the body assembly 26 (FIG. 2-4) described above between adjacent spinous processes 12 (FIG. 1-4) of the spinal column 14 (FIG. 1) of a patient. Again, the body assembly 26 is sized such that the body assembly 26 distracts the adjacent spinous processes 12 apart. The method also includes extending the plurality of attachment arms 38 (FIGS. 2-4) described above outwardly from the body assembly 26, the plurality of attachment arms 38 disposed about a portion of each of the adjacent spinous processes 12 and securely holding the body assembly 26 in place relative to each of the adjacent spinous processes 12 of the spinal column 14 of the patient. The body assembly 26 is disposed between adjacent spinous processes 12 of the spinal column 14 of the patient through the dilation tube 46 (FIG. 5) and the guide tube 50 (FIG. 5) described above.

Figure 7:
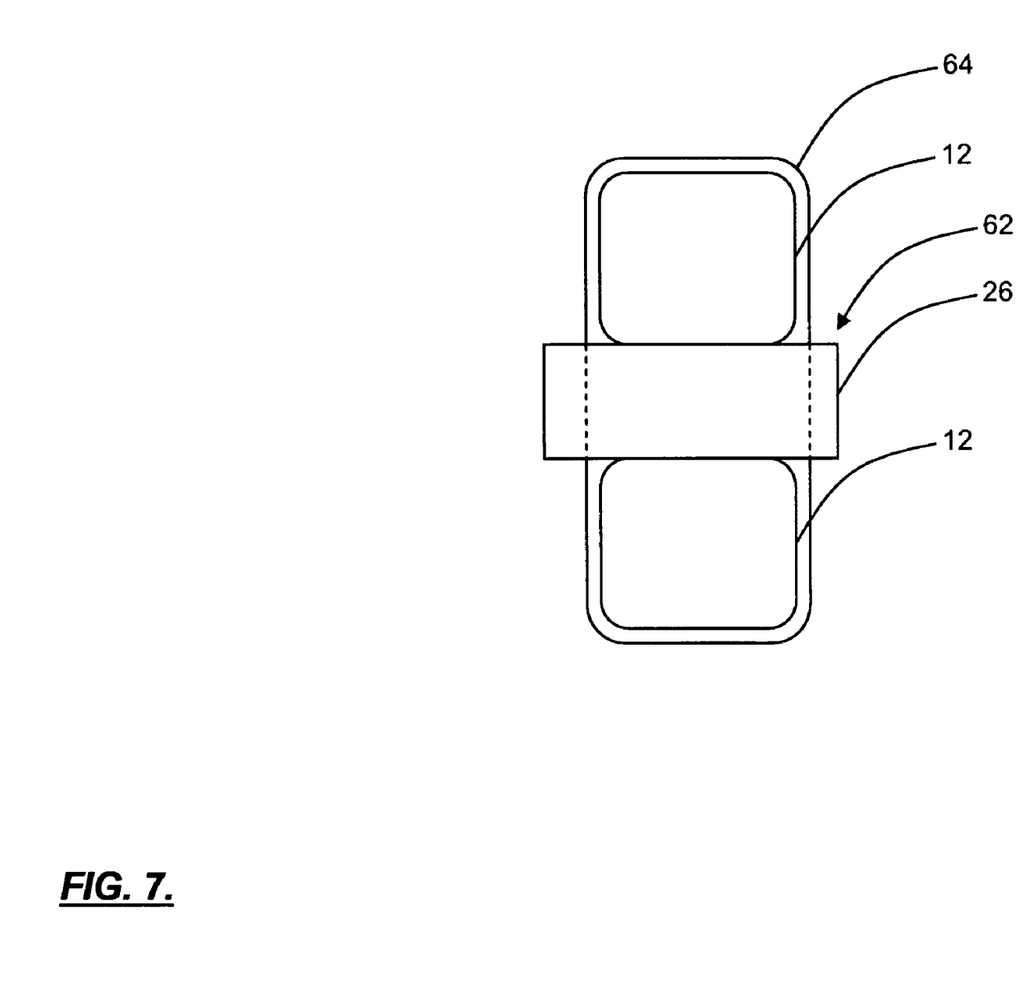
FIG. 7 a planar dorsal or anterior (back) view illustrating another exemplary embodiment of the interspinous distraction device of the present invention, the interspinous distraction device incorporating a stabilizing band.

Referring now to FIG. 7, in an alternative embodiment of the present invention, an interspinous distraction device 62 for treating such conditions as lumbar spinal stenosis and degenerative disc disease includes a body assembly 26 configured to be disposed between adjacent spinous processes 12 of the spinal column 14 (FIG. 1) of a patient. Again, the body assembly 26 is sized such that the body assembly 26 distracts the adjacent spinous processes 12 apart. The body assembly 26 may be the same as that described above, incorporating a plurality of attachment arms 38 (FIGS. 2-4), etc., or it may be a simple anchored or floating spacer device. The interspinous distraction device 62 also includes a band 64 configured to be disposed about the adjacent spinous processes 12 of the spinal column 14 of the patient and engage the body assembly 26, via crimping or otherwise. Thus, the band may initially be a simple strip of medically-implantable material or it may be a closed loop of medically-implantable material. The band 64 is sized such that the adjacent spinous processes 12 are stabilized with respect to one another. The band 64 maybe be substantially elastic or non-elastic and typically has a circumferential length of between about 60 mm and about 150 mm. The interspinous distraction device 62 is inserted into the spinal column 14 of the patient using an open procedure.

Figure 8:
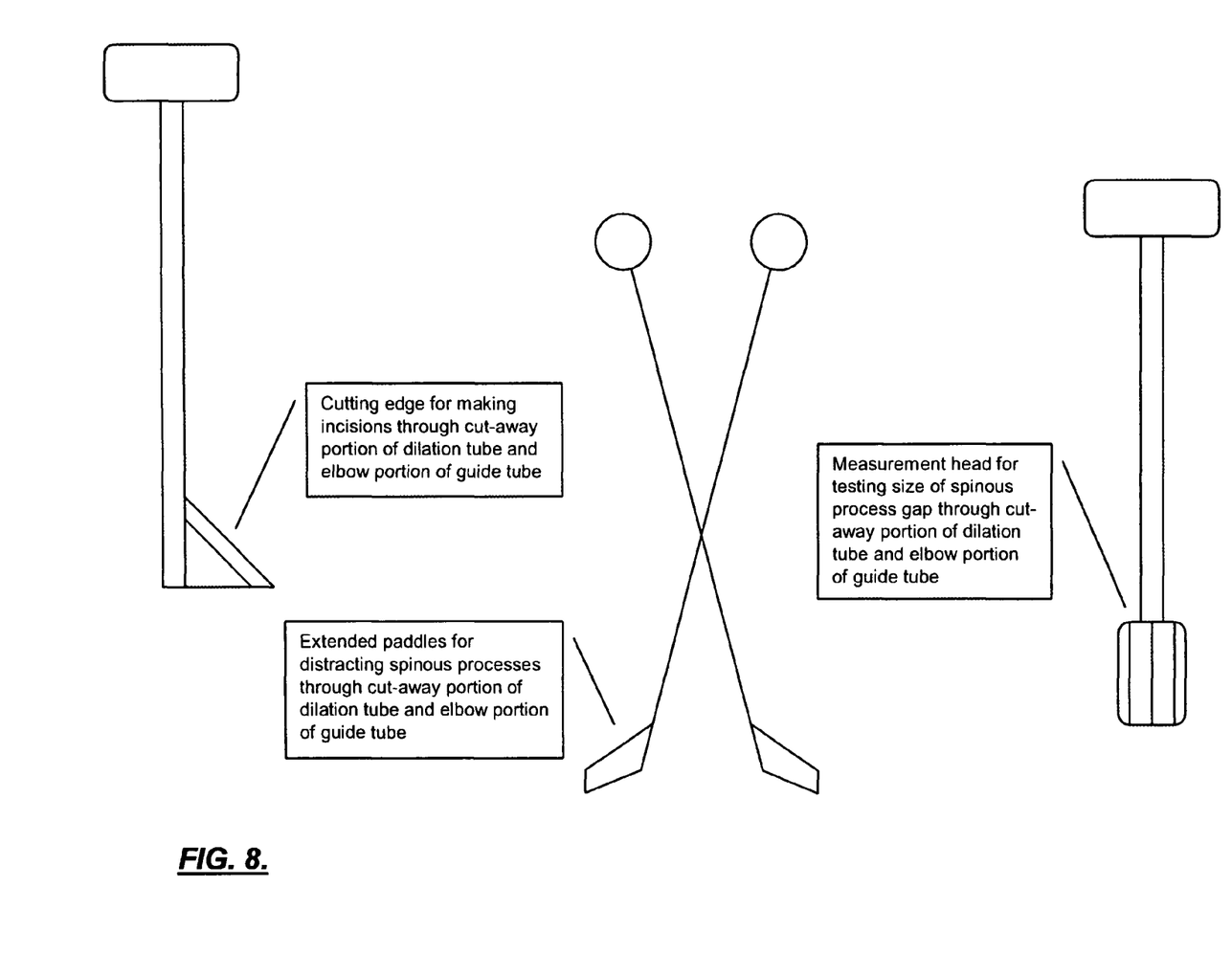
FIG. 8 is a planar view illustrating a plurality of enabling tools and instruments used in conjunction with the interspinous distraction devices of the present invention.

The present invention also contemplates a plurality of enabling tools and instruments. Such tools include extended handles and holding tools for feeding the interspinous distraction device 10 (FIGS. 2-4) through the dilation tube 46 (FIG. 5) and guide tube (FIG. 5) and anchoring the interspinous distraction device 10 between the adjacent spinous processes (FIG. 1). Such tools also include actuating and ratcheting tools for engaging the plurality of attachment arms 38 (FIGS. 2-4) of the interspinous distraction device 10 and placing the filler plug (not shown) in the interior void 30 (FIG. 2) defined by the circumferential wall 28 (FIGS. 2-4) of the body assembly 26 (FIGS. 2-4) of the interspinous distraction device 10, for example. Such tools further include visualization and cutting tools for preparing and distracting the area of interest for receiving the interspinous distraction device 10. Several of these tools are illustrated in FIG. 8.

Although the present invention has been illustrated and described with reference to preferred embodiments and examples thereof, it will be readily apparent to those of ordinary skill in the art that other embodiments and examples may perform similar functions and/or achieve similar results. All such equivalent embodiments and examples are within the spirit and scope of the present invention and are intended to be covered by the following claims.

What is claimed is:

1. A method for inserting an interspinous distraction device comprising:

disposing a body assembly between adjacent spinous processes of the spinal column of a patient, wherein the body assembly is sized such that the body assembly distracts the adjacent spinous processes apart, wherein the body assembly comprises a circumferential wall defining an interior void having laterally opposed open ends, and wherein the body assembly forms a plurality of openings extending through the circumferential wall; and extending a plurality of attachment arms outwardly from the body assembly through the plurality of openings extending through the circumferential wall such that a portion of the attachment arm is substantially surrounded by the circumferential wall of the body assembly, and at least one of the plurality of attachment arms passes through one of the plurality of openings alone without another one of the at least one of the plurality of attachment arms, wherein the plurality of attachment arms are disposed about a portion of each of the adjacent spinous processes and securely hold the body assembly in place relative to each of the adjacent spinous processes of the spinal column of the patient.

2. The method for inserting the interspinous distraction device of claim 1, wherein the body assembly has a height of between about 4 mm and about 20 mm, a width of between about 10 mm and about 25 mm, and a thickness of between about 10 mm and about 20 mm.

3. The method for inserting the interspinous distraction device of claim 1, wherein the body assembly has a shape selected from the group consisting of substantially rectangular, substantially square, substantially oval, substantially circular, and a combination thereof.

4. The method for inserting the interspinous distraction device of claim 1, further comprising disposing a filler plug within the interior void defined by the circumferential wall of the body assembly.

5. The method for inserting the interspinous distraction device of claim 1, wherein the exterior of the body assembly comprises one or more friction surfaces selected from the group consisting of one or more ridged surfaces, one or more grooved surfaces, one or more corrugated surfaces, one or more pebbled surfaces, and a combination thereof, the one or more friction surfaces configured to securely hold the body assembly in place relative to each of the adjacent spinous processes of the spinal column of the patient.

6. The method for inserting the interspinous distraction device of claim 1, wherein the exterior of the body assembly comprises one or more fin structures configured to securely hold the body assembly in place relative to each of the adjacent spinous processes of the spinal column of the patient.

7. The method for inserting the interspinous distraction device of claim 1, wherein each of the plurality of attachment arms has a length of between about 4 mm and about 20 mm.

8. The method for inserting the interspinous distraction device of claim 1, wherein each of the plurality of attachment arms is selectively extendable outwardly from/retractable inwardly into the body assembly.

9. The method for inserting the interspinous distraction device of claim 1, wherein the body assembly and the plurality of attachment arms each comprise a material selected from the group consisting of a medically-implantable, corrosion-resistant metal; a medically-implantable, corrosion-resistant metal alloy; a medically-implantable plastic; a medically-implantable ceramic; and a combination thereof.

10. The method for inserting the interspinous distraction device of claim 1, wherein the body assembly is disposed between adjacent spinous processes of the spinal column of the patient through a hollow dilation tube having a first end, a second end, a given cross-sectional shape, and a longitudinal axis, wherein the first end of the dilation tube comprises a cut-away portion for providing access from an interior portion of the dilation tube to an exterior portion of the dilation tube in a direction perpendicular to the longitudinal axis of the dilation tube.

11. The method for inserting the interspinous distraction device of claim 10, wherein the body assembly is disposed between adjacent spinous processes of the spinal column of the patient through a hollow guide tube having a first end, a second end, a given cross-sectional shape, and a longitudinal axis disposed concentrically within the dilation tube, wherein the first end of the dilation tube comprises an elbow portion for providing access from an interior portion of the guide tube to an exterior portion of the guide tube in a direction perpendicular to the longitudinal axis of the guide tube through the cut-away portion of the dilation tube.

* * * * *